US010779487B2

(12) United States Patent
Carver et al.

(10) Patent No.: US 10,779,487 B2
(45) Date of Patent: Sep. 22, 2020

(54) PLANT PROPAGATION

(71) Applicant: New Energy Farms Limited, Leamington (CA)

(72) Inventors: Paul Adrian Carver, Marlborough (GB); Dean William Tiessen, Marlborough (GB)

(73) Assignee: New Energy Farms Limited, Leamington (CA)

( * ) Notice: Subject to any disclaimer, the term of this patent is extended or adjusted under 35 U.S.C. 154(b) by 786 days.

(21) Appl. No.: 14/407,885

(22) PCT Filed: Jun. 12, 2013

(86) PCT No.: PCT/GB2013/051543
§ 371 (c)(1),
(2) Date: Dec. 12, 2014

(87) PCT Pub. No.: WO2013/186558
PCT Pub. Date: Dec. 19, 2013

(65) Prior Publication Data
US 2015/0150162 A1    May 28, 2015

(30) Foreign Application Priority Data

Jun. 12, 2012   (GB) .................................. 1210374.3

(51) Int. Cl.
A01H 4/00       (2006.01)
A01H 3/00       (2006.01)

(52) U.S. Cl.
CPC ............. *A01H 4/008* (2013.01); *A01H 3/00* (2013.01); *A01H 4/005* (2013.01)

(58) Field of Classification Search
None
See application file for complete search history.

(56) References Cited

U.S. PATENT DOCUMENTS 5,732,505 A * 3/1998 Carlson ................. A01H 4/006
                                                         47/57.6

FOREIGN PATENT DOCUMENTS

| CA | 2650762 A1    | 1/2003  |
| CN | 101258797 A   | 9/2008  |
| WO | 1995/020645 A1| 8/1995  |
| WO | 1998/046727 A1| 10/1998 |
| WO | 2007/072046 A1| 6/2007  |
| WO | 2007/090624 A2| 8/2007  |
| WO | 2009/021274 A1| 2/2009  |
| WO | 2010/102220 A1| 9/2010  |
| WO | 2011/019984 A2| 2/2011  |
| WO | 2011/120035 A1| 9/2011  |

OTHER PUBLICATIONS

Vogel et al 1998 (PNAS 95: p. 4766-4771).*
Gopala et al 2010 (Scientia Horticulturae 125: p. 761-766).*
Sato et al 1986 (American Journal of Pathology 125: p. 431-435).*
Kapoor and Rao 2006 (Plant Cell Tissue and Organ Culture 85: p. 211-217).*
Rodriguez-Leyva et al 2010 (Nutrition and Metabolism 7:32 p. 1-9).*
Decout et al 1994 (Journal of Experimental Botany 45:281 p. 1859-1865).*
Joyce et al 2003 (Plant Cell, Tissue, and Organ Culture 74: p. 101-121).*
Al-Khateeb 2008 (Bioresource Technology 99: p. 6550-6555).*
Examination Report, European Patent Application No. 13739482.1, dated Feb. 3, 2016, 5 pages.
Aminah A., et al., "Techniques for Rapid Vegetative Multiplication for Pasture Species and Commercial Production." Proc. of First Meeting of the Regional Working Group on Grazing and Feed Resources of Southeast Asia, 1989, pp. 166-175.
Office Action, Colombian Patent Application No. 20150004720, 18 pages (with English translation).
Motion to Oppose Invention Patent, Costa Rica Application No. 2015-0011, 7 pages.
Brischia, Romina, et al., "Micropropagation and synthetic seed in M.26 apple rootstock (II): A new protocol for production of encapsulated differentiating propagules." Plant Cell, Tissue and Organ Culture, 2002, vol. 68, pp. 137-141.
Gardi, T., et al., "Effect of bead nutrient composition on regrowth of stored vitro-derived encapsulated microcuttings of different woody species." J. Microencapsulation, 1999, vol. 16, No. 1, pp. 13-25.
Germana, Maria Antonietta, et al., "Organogenesis and encapsulation of in vitro-derived propagules of Carrizo citrange [*Citrus sinensis* (L.) Osb. x Poncirius trifoliata." Plant Cell, Tissue and Organ Culture, 2011, vol. 106, pp. 299-307.
Godbole, Savita, et al., "Somatic embryogenesis and its conversion into plantlets in a multipurpose bamboo, Dendrocalamus hamiltonii Nees et Am. Ex Munro." Current Science, Oct. 10, 2002, vol. 83, No. 7, pp. 885-889.
Hammatt, N., "Progress in the biotechnology of trees." World Journal of Microbiology and Biotechnology, 1992, vol. 8, pp. 369-377.
Kapoor, Priyanka, et al., "In vitro rhizome induction and plantlet formation from multiple shoots in Bambusa bambos var. gigantea Bennet and Gaur by using growth regulators and sucrose." Plant Cell, Tissue and Organ Culture, 2006, vol. 85, pp. 211-217.
Lo-Apirukkul, Sureerat, et al., "Micropropagation of a Thai medicinal plant for women's health, Curcuma comosa Roxb., via shoot and microrhizome inductions." Journal of Natural Medicine, 2012, vol. 66, pp. 265-270.

(Continued)

*Primary Examiner* — Matthew R Keogh
(74) *Attorney, Agent, or Firm* — Fitch Even Tabin & Flannery LLP

(57)    ABSTRACT

The present application relates generally to the field of plant propagation. In particular, the present invention relates to a method for the propagation of vegetatively reproducing plants and plants and plant parts produced by such methods. The invention also provides encapsulated propagules. The invention also provides various end uses for the encapsulated propagules and for plants grown from the same. The invention also provides a method for the modification of the architecture of rhizomes and rhizomes having modified architecture and a method for the modification of the architecture of stem cuttings and stem cuttings having modified architecture. The invention also provides a coating for a propagule and a propagule coated therewith.

30 Claims, 2 Drawing Sheets

(56) References Cited

OTHER PUBLICATIONS

Nayak, Sanghamitra., "In vitro multiplication and microrhizome induction in Curcuma aromatica Salisb." Plant Growth Regulation, 2000, vol. 32, pp. 41-47.
Piccioni, Emanuele, et al., "Encapsulation of micropropagated buds of six woody species." Plant Cell, Tissue and Organ Culture, 1995, vol. 42, pp. 221-226.
International Search Report and Written Opinion, International Patent Application No. PCT/GB2013/051543, completion date Sep. 18, 2013, 13 pages.
British Search Report, Application No. GB1310444.3, dated Jan. 17, 2014, 4 pages.

* cited by examiner

PLANT PROPAGATION

The present application relates generally to the field of plant propagation. In particular, the present invention relates to a method for the propagation of vegetatively reproducing plants and plants and plant parts produced by such methods. The invention also provides encapsulated propagules. The invention also provides various end uses for the encapsulated propagules and for plants grown from the same. The invention also provides a method for the modification of the architecture of rhizomes and rhizomes having modified architecture and a method for the modification of the architecture of stem cuttings and stem cuttings having modified architecture. The invention also provides a coating for a propagule and a propagule coated therewith.

BACKGROUND

Recently, there has been much interest in alternative energy sources that can reduce our reliance on traditional energy sources such as coal, oil and nuclear power. One such alternative energy source is bio-fuels, which is fuel derived from crops (energy crops) which can be burned to produce heat and electricity or treated with enzymes to produce sugars that can be used to produce ethanol or hydrogen. *Miscanthus* is an example of a perennial grass that has been identified as an energy crop due to its high biomass yields.

There are a number of *Miscanthus* species, but currently the most productive clone is a sterile hybrid, *Miscanthus* x *giganteus*, resulting from a natural cross between *M. sacchariflorus* and *M. Sinensis*. *Miscanthus* is a seed-bearing grass but the hybrid *M.* x *giganteus* is a triploid which is therefore sterile and does not produce seed. It can therefore only be multiplied by vegetative means which has severely restricted its commercial introduction.

The main concern with seeded varieties of *Miscanthus* is their potential to become invasive, however the alternative to seeded varieties is to rely on vegetative propagation which is largely inefficient. Conventional means for the vegetative propagation of *Miscanthus* involves planting rhizome cuttings produced from dedicated multiplication crops, rhizomes being underground stems. As commercial *Miscanthus* crops develop over 20 or more years, their root complexes can become rather large and woody. Rhizomes that are suitable for establishing new crops are usually specifically produced in multiplication fields and are often planted at high density and harvested after 2-4 years. These conventional rhizomes are uneven in shape and can often have numerous root hairs and adventitious roots making them difficult to process using conventional farming equipment and difficult to store and handle due to the tangling of the root hairs and due to their large, uneven and bulky nature. Rhizome cuttings are obtained from these "root complexes", which are usually about 12-15 cm long and weigh about 50 g including the surrounding soil. Although these rhizomes look robust, they are rather sensitive to dehydration and therefore require careful storage and handling. The aforementioned factors make the multiplication of *Miscanthus* relatively expensive compared to other crops. For example, under typical growing conditions in Europe, the multiplication ratio of *Miscanthus* rhizomes is around 3-5 fold in one growing season, meaning than one rhizome will produce a maximum of five rhizomes after one year's growth. This is in contrast to cereals with a multiplication ratio of up to 80 fold and oilseed rape which has a multiplication rate of over 5,000 fold. Similarly, the costs of planting conventional *Miscanthus* rhizomes are also high compared with the costs of cleaning, processing and planting seeded crops.

Attempts have been made to solve the aforementioned problems by adapting the planting equipment to suit the rhizomes, including the introduction of precision planting, both of which have increased the reliability of crop establishment. However, to date, no attempts have been made to adapt the rhizome itself to better suit conventional farming apparatus.

Many of the crops (perennial grasses) required for producing feedstock for fuel, feed and fibre do not posses rhizomes at all or not in sufficient quantities and therefore require stem propagation. However, similar problems exist with plant propagation based on stem cuttings. For example, sugarcane is an economically important crop for sugar production and for bio-fuel production, but production of sugarcane is labour-intensive and reliant on the use of specialist machinery. Cultivation of sugarcane involves a fairly lengthy process of about 2 years for the production of cane seed using micro-propagation techniques, followed by testing and breeding to develop new sugarcane cultivars. With high disease pressure, it can take up to five years for new cultivars to reach the market. The multiplication of sugarcane from seed cane then begins, a process which typically takes about 3 years before commercial production can begin. Typically, about 20% of the total growing area is reserved for multiplication, meaning that about 20% of the land is tied up for at least 3 years, if not continuously, for successive cycles of multiplication. The multiplication ratios over the 3 year period are also relatively inefficient showing around an 8-fold increase.

Some efficiency gains have been reported for rhizomatous crops such as turmeric and bamboo from the use of micro-propagation techniques. For example, a publication in the name of Nayak (Plant Growth Regulation 32: 41-47, 2000) describes the in vitro multiplication of turmeric using tissue culture techniques and further describes the induction of micro-rhizomes using sucrose and 6-benzyladenine and a specified photoperiod. Similarly, Lo-apirukkul et al., (J Nat Med (2012) 66: 265-270) describe the micro-propagation of a Thai medicinal plant, *Curcuma comosa* Roxb., and the induction of micro-rhizomes. The in vitro induction of rhizomes in bamboo has been reported by Kapoor and Rao (Plant Cell, Tissue and Organ Culture (2006) 85: 211-217). The efficiency gains reported in the prior art methods involving the use of in vitro micro-propagation techniques show an improvement of about seven-fold compared to conventional methods. There therefore remains a need for ever more efficient methods for the propagation of vegetatively reproducing plants.

One of the major obstacles preventing wider cultivation of *Miscanthus* and other such crops is the inefficient propagation discussed above due, at least in-part, to its vegetative means for reproduction. There therefore remains a need for a more economically efficient means for the establishment of *Miscanthus* and other vegetatively reproducing crops.

SUMMARY OF THE INVENTION

The present invention aims to solve some of the aforementioned problems associated with the propagation of *Miscanthus* and other vegetatively reproducing plants, by providing a more efficient plant propagation process and by providing an encapsulated propagule which is in a form ready for planting.

The efficiency gains obtained by performing the methods of the invention give an improvement, depending on the plant in question, of between about 50-fold to about 200-fold compared to the prior art methods, which show an improvement of about seven-fold compared to conventional techniques.

According to the present invention, there is therefore provided a method for the propagation of a vegetatively reproducing plant, comprising the steps of:
(i) micro-propagation of plant material from a vegetatively reproducing plant followed by multiplication to produce plantlets;
(ii) contacting the plantlets or a part thereof from step (i) with at least one plant hormone and growing the plantlets and harvesting mini rhizomes or mini stem cuttings therefrom;
(iii) substantially encapsulating the mini rhizomes or mini stem cuttings produced from step (ii) in a plant growth medium.

The present invention also provides encapsulated mini rhizomes and encapsulated mini stem cuttings, which are collectively referred to herein as "encapsulated propagules". Also provided herein are various uses for the encapsulated propagules and various uses for the plants obtained therefrom.

The present invention also provides a biodegradable polymer for the coating of a propagule and propagules coated in the same.

Also provided is a method for altering the architecture of a rhizome or a stem cutting using plant hormones and/or by performing the methods of the invention.

DETAILED DESCRIPTION OF THE INVENTION

The inefficiencies associated with conventional processes for the propagation of *Miscanthus* are overcome in the process of the present invention, which results in a greater productivity and in a more uniform end-product. Furthermore, the methods of the invention are more amenable to automation resulting in further efficiency gains compared to conventional processes. Furthermore, due to the more uniform size and shape of the mini rhizomes and mini stem cuttings produced by the methods, conventional agricultural equipment may readily be used in the planting process after minimal adaptation, where necessary, thereby removing any additional expense associated with having to produce customized equipment.

According to the present invention, there is therefore provided a method for the propagation of a vegetatively reproducing plant, comprising the steps of:
(i) micro-propagation of plant material from a vegetatively reproducing plant followed by multiplication to produce plantlets;
(ii) contacting the plantlets or a part thereof from step (i) with at least one plant hormone and growing the plantlets and harvesting mini-rhizomes or mini stem cuttings therefrom;
(iii) substantially encapsulating the mini-rhizomes or mini stem cuttings produced from step (ii) in a plant growth medium.

Micro-propagation is a standard, well known horticultural technique used for the rapid bulking up of large numbers of plantlets. The micro-propagation described in stage (i) of the method aims at producing large quantities of material suitable for entering stage (ii) of the method. The micro-propagation techniques used may be any conventional micro-propagation technique, such as tissue culture or rooted stem cuttings.

The micro-propagation results in plantlets which are ready to be multiplied, typically in a greenhouse. Conventional means for plant multiplication are used for this stage of the method. The greenhouse multiplication of the plantlets typically results in a 20-30 fold increase every 2-3 months. In the case of *Miscanthus* and *Arundo donax*, the micropropagation and multiplication results in every one plant generating about 10 plants in about an 8 week cycle; those 10 plants can then in turn generate about 100 plants in a further cycle of about 8 weeks.

Advantageously, micro-propagation followed by multiplication can result in every 1 (one) plant generating 10 million plantlets, plug plants or bare root cuttings (which refer to individual stems which can be separated from larger plants) in less than 6 months or in less than 8 months or in less than 10 months or in less than 12 months or in less than 14 months or in less than 16 months or in less than 18 months, depending on the plant in question.

Advantageously, micro-propagation followed by multiplication results in a decreased rate of mutation compared to conventional micropropagation, which again contributes to the overall efficiency gains brought about by performing the methods of the invention.

The resulting plantlets are then ready for the hormone treatment in stage (ii) of the process.

The terms "plantlet", "plug plant" and "bare root cutting" are used interchangeably herein and are taken to mean the small plants produced following the micro-propagation and multiplication techniques of stage (i) of the method. The size of the plantlet will vary depending on the plant being propagated, and a skilled person will have at his or her disposal suitable means for generating plantlets from any given plant. In the case of *Miscanthus*, the plantlets are typically in the range of at least 2-5 cm in length.

The term "rhizome" as used herein is used in its conventional sense to refer to an underground stem of a plant, which typically produces roots and shoots. The term "rhizomatous" plant as used herein refers to any plant capable of producing a rhizome. The term "mini-rhizome" is a term known in the art and refers to a whole rhizome from any given plant species which is about 10% of the size of a typical whole rhizome for that plant species, preferably about 5% of the size of a typical whole rhizome for that plant species. For example, a typical whole rhizome from *Miscanthus* is about 50 g in weight and between about 12 to 15 cm in length, whereas a mini-rhizome from the same plant species is typically about 5 g in weight, preferably about 4 g or 3 g or 2 g in weight and between about 2 to 5 cm in length, preferably between about 1 to 2 cm in length.

The term "stem cutting" as used herein is used in its conventional sense where a piece of any given parent plant is removed and encouraged to grow as an independent plant by placing the removed plant piece on a suitable growth medium, such as one or more of the following: soil, compost, potting mix, rock wool, perlite, vermiculite, coir, expanded clay pellets, hydrogel and water, which facilitates the growth of new roots and/or stems, which enable the stem cutting to become a plant independent of the source plant. The term "mini stem cutting" as used herein refers to a stem cutting from any given plant species which is about 10% of the size of a typical stem cutting for that plant species, preferably about 5% of the size of a typical stem cutting for that plant species. For example, a typical stem cutting from *Arundo donax* is about 100 g in weight and between about 40 to 60 cm in length, whereas a mini stem cutting from the same plant species is typically about 10 g in weight, preferably about 4 g or 3 g or 2 g in weight and between about 2 to 4 cm in length. In the case of sugarcane, a conventional stem cutting is 30 to 40 cm in length, whereas a mini stem cutting from the same sugarcane species is typically between about 2 to 4 cm in length.

The plantlets produced in stage (i) of the process are then subjected to stage (ii) of the process, which comprises hormonal treatment of the plantlets with cytokinin(s) and/or auxin(s). Any one given plant hormone is applied at a rate of less than about 1000 ppm, less than about 900 ppm, less than about 800 ppm, less than about 700 ppm, less than about 600 ppm, less than about 500 ppm, less than about 400 ppm, less than about 300 ppm, less than about 200 ppm, less than about 100 ppm, less than about 90 ppm, less than about 80 ppm, less than about 70 ppm, less than about 60 ppm, less than about 50 ppm, less than about 40 ppm, less than about 30 ppm, less than about 20 ppm or less than about 10 ppm.

The cytokinin may be selected from the group consisting of kinetin, zeatin, 6-benzylaminopurine, diphenyl urea and thidiazuron (TDZ). The auxin may be selected from the group consisting of indole-3-actetic acid (IAA), 4-chloroindole-3-acetic acid (4-Cl-IAA), 2-phenylacetic acid (PAA) and indole-3-butyric acid (IBA). A combination of benzylaminopurine, TDZ and IAA is preferred in the case of *Miscanthus* propagation. Preferably, the benzylaminopurine, TDZ and IAA are each applied at a rate of less than about 1000 ppm, less than about 900 ppm, less than about 800 ppm, less than about 700 ppm, less than about 600 ppm, less than about 500 ppm, less than about 400 ppm, less than about 300 ppm, less than about 200 ppm, less than about 100 ppm, less than about 90 ppm, less than about 80 ppm, less than about 70 ppm, less than about 60 ppm, less than about 50 ppm, less than about 40 ppm, less than about 30 ppm, less than about 20 ppm or less than about 10 ppm. The combinations and concentrations of plant hormones may readily be optimized, if necessary, by one skilled in the art depending on the plant to be propagated.

According to a preferred feature of the present invention, after stage (i) of the process and before, after or during the hormone treatment of stage (ii), but before the harvesting of mini rhizomes or mini stem cuttings, the plants may be subjected to a temporary abiotic or mechanical stress.

The abiotic stress may comprise subjecting the growing plant to any temporary environmental change compared to the normal growth conditions for the plant in question. For example, the stress may be any one or more of: (i) an osmotic stress (which may be caused by limited or excess salt or water compared to the normal levels of salt or water); (ii) a temperature stress (which may be caused by exposure of the plant to excessive heat or cold compared to normal growth conditions for the plant in question); (iii) a nutrient stress (which may be caused by a lack of nitrogen, phosphorous, sulphur etc.); or (iv) an oxidative stress. The exposure of the plants to the temporary abiotic and/or mechanical stress serves to encourage more bud formation.

The mechanical stress refers to any non-environmental stress resulting from a physical action to a plant, such as cutting parts of the plant. Preferably, the aboveground parts of the plant are cut back to a point just above a node.

Reference herein to a "temporary" stress is taken to mean exposure to a non-continuous stress, which may involve exposure of the plant to any one or more given stresses at intermittent periods. For example, the intermittent periods of stress may be 1, 2, 3, 4 or 5 or more separate occasions of exposure of the plant to a stress in between non-stress periods.

Stage (ii) of the process (contacting the plantlets with at least one plant hormone), which may or may not comprise exposure of the plants to an abiotic and/or mechanical stress, can last from between about 12 and 24 weeks depending on the plant in question and depending on whether sufficient buds have formed.

The contacting of the plantlets to at least one plant hormone may occur before, after or during exposure of the plants to a temporary abiotic or mechanical stress. Preferred plant hormones include benzylaminopurine, TDZ and IAA, one or more of which may be applied at a rate of <1000 ppm (less than one thousand parts per million).

Therefore, a preferred method for the propagation of a vegetatively reproducing plant comprises the steps of:
(i) micro-propagation of plant material from a vegetatively reproducing plant followed by multiplication to produce plantlets;
(ii) contacting the plantlets or a part thereof from step (i) with at least one plant hormone;
(iii) exposing the plantlets before, after or during step (ii) above to an abiotic or mechanical stress;
(iv) growing the plantlets and harvesting mini rhizomes or mini stem cuttings therefrom;
(v) substantially encapsulating the mini rhizomes or mini stem cuttings produced from step (iv) in a plant growth medium.

The hormone-treated plants are then grown in a field or greenhouse setting under optimal growth conditions. In the case of *Arundo donax* or other plants produced from stem cuttings, this growth phase may span a period of about 12 months. Shoots emerging from the new buds are removed and cut (by machine or hand) into short lengths resulting in mini stem cuttings.

In the case of *Miscanthus*, this growth phase may span a period of about 12 months or until the size of the plant is about 20 cm in length and the rhizomes are between about 2 to 5 g in weight and/or until the bud capacity of the rhizomes is around 20 buds per rhizome.

The rhizomatous plant material growing in the field or greenhouse may then be subjected to a light shredding or separation of the root complex in order to separate out the mini rhizomes therefrom. Advantageously, this shredding or separation process may be automated to directly take plant material from the field or greenhouse and to separate out the mini rhizomes from the root complex ready for the encapsulation stage.

The hormonal treatment followed by the growth cycle in the field or greenhouse leads to the generation of mini rhizomes from the plantlets of stage (i). Advantageously, in the case of *Miscanthus* propagation, the mini rhizomes are around 2 to 5 g in weight compared to the about 30 to 50 g weight of rhizomes produced by conventional production methods. A further advantage is that the *Miscanthus* mini rhizomes are also more uniform in shape and size than the rhizomes of conventionally-produced *Miscanthus* plants, meaning that they can be planted with minimal adaptation (where necessary) of available agricultural machinery, thereby avoiding the expense associated with providing specially adapted or custom-made agricultural machinery.

The small, uniformly-shaped mini rhizomes or mini stem cuttings resulting from stage (ii) of the method are then in a form ready for encapsulation. The encapsulation process may advantageously be automated. The combined automation of the shredding (in the case of rhizomatous plants) and encapsulation processes will contribute towards further efficiency gains.

The mini rhizome or mini stem section or cutting may advantageously be encapsulated in any plant growth medium, such as compost, potting mix, peat, hydrogel, soil, rock wool, perlite, vermiculite, foam, syrofoam, pumice, coir, expanded clay pellets etc. The resulting encapsulated rhizome or encapsulated mini stem cutting propagule is a stable planting unit of less than about 10 g, or less than about 15 g for some crops, and is in a form ready for precision planting using minimally adapted conventional farming equipment or ready for storage until required.

The encapsulation material may also comprise compounds, such as plant hormones (such as cytokinins or auxins), plant growth regulators, mycorrhiza, endophytic organisms, symbiotic organisms or other beneficial organisms, surfactants, gels, fungicides, nematicides, insecticides, organic and inorganic nutrients, water, polymer and organic-based super absorbents and stabilization compounds etc. to aid the storage of the mini rhizomes and mini stem cuttings so as to prevent any loss of material due to deterioration and to enhance the survival and performance of the propagules once they are planted in the field.

According to a preferred feature of the present invention, the encapsulated material is then substantially coated in a biodegradable polymer, which preferably has a melting point of between 30 to 65° C.

Preferably the polymer is selected from one or more of wax, polyester, petroleum-based paraffin or plastic, polysaccharide or any plant-based plastic.

Preferably, the coating also comprises a fibre component comprising at least up to 20%, at least up to 30%, at least up to 40%, at least up to 50%, at least up to 60%, at least up to 70%, at least up to 80% or at least up to 90% of the coating.

The fibre may be one or more of the following: (i) fibre from agricultural biomass residue (for example, cereal straw, cotton, peanut hulls, soy straw, corn fodder); (ii) dedicated fibres (for example, *Miscanthus, Arundo*, sugarcane, bagasse, hemp, Kenaf); (iii) processed fibres (for example, paper, recycled cardboard, wood flour, wood saw dust); and (iv) artificial or processed fibres (for example, nylon, polyester, cotton).

The coating may also comprise fungicides, endophytic organisms, plant nutrients, hormones, dyes or other means for identification, such as barcodes or transponders or the like, to aid sorting.

The coating is applied to the encapsulated propagule by dipping (at least once) or by co-extrusion or by thermally forming the coating around the propagule. The coating covering the propagule is less than 1 mm (millimetre) thick, preferably less than 0.5 mm thick.

According to a preferred embodiment of the present invention, there is therefore provided a method for the propagation of a vegetatively reproducing plant, comprising the steps of:
(i) micro-propagation of plant material from a vegetatively reproducing plant followed by multiplication to produce plantlets;
(ii) contacting the plantlets or a part thereof from step (i) with at least one plant hormone and growing the plantlets and harvesting mini-rhizomes or mini stem cuttings therefrom;
(iii) substantially encapsulating the mini-rhizomes or mini stem cuttings produced from step (ii) in a plant growth medium; and
(iv) substantially coating the encapsulated mini rhizome or mini stem cutting of step (iii) in a biodegradable polymer.

According to a further preferred embodiment of the present invention, there is provided a method for the propagation of a vegetatively reproducing plant, comprising the steps of:
(i) micro-propagation of plant material from a vegetatively reproducing plant followed by multiplication to produce plantlets;
(ii) contacting the plantlets or a part thereof from step (i) with at least one plant hormone;
(iii) exposing the plantlets before, after or during step (ii) above to an abiotic or mechanical stress;
(iv) growing the plantlets and harvesting mini rhizomes or mini stem cuttings therefrom;
(v) substantially encapsulating the mini rhizomes or mini stem cuttings produced from step (iv) in a plant growth medium; and
(vi) substantially coating the encapsulated mini rhizome or mini stem cutting of step (v) in a biodegradable polymer.

A preferred method for the propagation of a rhizomatous plant comprises the steps of:
(i) micro-propagation of plant material from a rhizomatous plant followed by multiplication to produce plantlets;
(ii) contacting the plantlets or a part thereof from step (i) with at least one plant hormone and growing the plantlets;
(iii) exposing the plantlets before, after or during step (ii) above to an abiotic or mechanical stress;
(iv) growing the plantlets and harvesting mini rhizomes therefrom;
(v) shredding or separation of the root complex to separate out the mini rhizomes therefrom;
(vi) substantially encapsulating the mini rhizomes produced in step (iv) or (v) in a plant growth medium; and optionally
(vii) substantially coating the encapsulated mini rhizome of step (vi) in a biodegradable polymer.

The preferred aspects of steps (i) to (vii) above are as described hereinabove.

A preferred method for the propagation of a plant from a stem cutting comprises the steps of:
(i) micro-propagation of plant material from a plant stem followed by multiplication to produce plantlets;
(ii) contacting the plantlets or a part thereof from step (i) with at least one plant hormone and growing the plantlets;
(iii) exposing the plantlets before, after or during step (ii) above to an abiotic or mechanical stress;
(iv) growing the plantlets and harvesting mini stems from the shoots produced; (v) substantially encapsulating the mini stems produced in step (iv) in a plant growth medium; and optionally
(vi) substantially coating the encapsulated mini stem of step (v) in a biodegradable polymer.

The preferred aspects of steps (i) to (vi) above are as described hereinabove.

Advantageously, the methods of the invention may be applied to any plant capable of vegetative reproduction. In particular, the methods of the invention are particularly suited to rhizomatous and stem propagated plants. For example, the methods of the invention are particularly suited to energy grasses, such as *Miscanthus* (elephant grass), *Pennisetum purpureum* (napier grass), *Panicum virgatum*

(switch grass), energy cane (the *Saccharum* complex), *Arundo donax* (Giant Reed), Sugarcane, *Bambusa* (bamboo), *Curcuma, Humulus* (hop), asparagus, *Zingiber* (ginger), iris, genus *Erianthus, Fallopia sachalinensis* (Igniscum), *Ipomoea batatas* (sweet potato) and wasabi. In addition there are applications for other food and medicinal crops propagated using rhizomes or stems, such as strawberry (genus *Fragaria*), the medicinal herb nettle (genus *Urtica*) and turmeric.

*Arundo donax* (giant reed), *Pennisetum purpureum* (napier grass), energy cane, *Saccharum officinarum* (sugar cane), *Hevea* (rubber) and *Manihot* (cassava), for example, are more suited to multiplication using stem cuttings. When multiplying using stem cuttings, the plantlets, derived from micro-propagation are planted and grown to a suitable height and any aboveground growth is cut back to a point just above a node. This procedure encourages more bud formation which may be further stimulated by the application of cytokinins and auxins. The shoots emerging from the new buds are removed and cut up by machine into short lengths to form mini stem cuttings which are then ready to be encapsulated. Although not all of the stem cuttings that are produced will contain buds, the multiplication rate that is achieved is many times greater than would be achieved by conventional procedures.

According to another aspect of the present invention, there is provided a substantially encapsulated mini rhizome or substantially encapsulated mini stem cutting produced by the method according to the invention. The encapsulated mini rhizome or encapsulated mini stem cutting may be substantially coated in a biodegradable polymer.

The present invention also provides a planting unit weighing less than about 25 g, or less than about 20 g, or less than about 15 g or less than about 10 g, or less than about 5 g, or less than about 2 g, comprising a substantially uniformly-shaped mini rhizome or mini stem cutting substantially contained within a plant growth medium and optionally coated in a biodegradable polymer. The weight of the planting unit described above does not include the growth medium. In one embodiment of the present invention, the planting unit comprises a rhizome from a *Miscanthus* plant, energy cane, *Arundo donax* or sugarcane plant.

The invention also provides a method for the production of plants, comprising the steps of growing an encapsulated mini rhizome or mini stem cutting produced by the methods according to the invention. Also provided are plants obtainable from such an encapsulated mini rhizome or mini stem cutting and progeny and ancestors thereof.

Advantageously, plants produced from the mini stem cuttings or mini rhizomes produced by the methods according to the present invention have increased vigour. Taking *Miscanthus* as an example, this is manifested by an increase in the number of tillers (200 to 400% increase); increased height (up to a 30% increase); increased root volume (up to 300% increase); increased belowground buds (up to a 400% increase); increased canopy closure (up to a 200% increase); and increased leaf area (up to an 800% increase).

In the case of *Miscanthus*, 60 to 90 days after germination, the plants produced by the methods of the invention resemble conventionally produced plants that are one year or older.

According to the present invention, there is provided use of an encapsulated mini rhizome or mini stem cutting, or plants produced therefrom, in increasing plant vigour relative to conventionally grown plants of the same species.

Advantageously, the mini stem cuttings and mini rhizomes produced by the methods of the present invention offer starting material for plant propagation having the same growth capacity but of greatly reduced weight compared to conventional starting material, thereby saving transportation costs, storage and handling costs etc. For example, the weight of the starting material (mini stem cuttings and mini rhizomes) will be about 0.25 tonnes per hectare compared to 1.5 tonnes per hectare in the case of conventionally grown *Miscanthus*, 6 tonnes per hectare for conventionally grown Napier grass and 10 tonnes per hectare for conventionally grown sugarcane.

Advantageously, the mini stem cuttings or mini rhizomes produced by the methods of the present invention allow the harvest cycle of the crop plants grown therefrom to be shortened compared to the harvest cycle of the same plant grown by conventional methods. The mini stem cuttings or mini rhizomes produced by the methods of the present invention offer multiple planting windows compared to the planting window for the same plant grown by conventional methods. According to the present invention, there is provided use of an encapsulated mini rhizome or mini stem cutting or plants produced therefrom in altering the harvest cycle of a plant.

The plants produced by growing an encapsulated mini rhizome or mini stem cutting may also find use in the production of bio-fuels or bio-ethanol. According to the present invention, there is provided use of an encapsulated mini rhizome or mini stem cutting or plant produced therefrom in biofuel or bioethanol production.

Advantageously, the mini stem cuttings and mini rhizomes produced by the methods of the present invention may find use in bioremediation applications for cleaning up areas having contaminated water. According to the present invention, there is provided use of an encapsulated mini rhizome or mini stem cutting or plant produced therefrom in bioremediation.

According to another aspect of the present invention, there is provided a method for altering rhizome architecture, comprising the steps of:
(i) micro-propagation of plant material from a rhizomatous plant to produce plantlets; and
(ii) contacting the plantlets from step (i) with plant hormones selected from the group consisting of benzylaminopurine, TDZ and IAA;
(iii) obtaining substantially uniformly-shaped mini rhizomes weighing less than about 25 g.

The aforementioned method for altering rhizome architecture may also comprise the additional steps of shredding and/or encapsulation of the rhizomes as described hereinabove.

A preferred method for altering rhizome architecture comprises the steps of:
(i) micro-propagation of plant material from a rhizomatous plant followed by multiplication to produce plantlets;
(ii) contacting the plantlets or a part thereof from step (i) with a plant hormone selected from the group consisting of benzylaminopurine, TDZ and IAA and growing the plantlets;
(iii) exposing the plantlets before, after or during step (ii) above to an abiotic or mechanical stress;
(iv) growing the plantlets and harvesting mini-rhizomes therefrom;
(v) shredding or separation of the root complex to separate out the mini rhizomes therefrom;
(vi) obtaining substantially uniformly-shaped mini rhizomes weighing less than about 25 g.

According to another aspect of the present invention, there is provided a method for altering stem architecture, comprising the steps of:
(i) micro-propagation of plant material from a plant stem to produce plantlets; and
(ii) contacting the plantlets from step (i) with a plant hormone selected from the group consisting of benzylaminopurine, TDZ and IAA;
(iii) obtaining substantially uniformly-shaped mini stems weighing less than about 25 g.

A preferred method for altering stem architecture comprises the steps of:
(i) micro-propagation of plant material from a plant stem followed by multiplication to produce plantlets;
(ii) contacting the plantlets or a part thereof from step (i) with a plant hormone selected from the group consisting of benzylaminopurine, TDZ and IAA and growing the plantlets;
(iii) exposing the plantlets before, after or during step (ii) above to an abiotic or mechanical stress;
(iv) growing the plantlets and harvesting mini stems from the shoots produced;
(v) obtaining substantially uniformly-shaped mini stems weighing less than about 25 g.

The present invention provides mini rhizomes and mini stem cuttings obtainable by the methods described herein. The method for altering rhizome or mini stem architecture results in mini rhizomes or mini stem cuttings weighing less than about 25 g or weighing less than about 20 g or weighing less than about 15 g or weighing less than about 10 g or weighing less than about 5 g or weighing less than about 2 g.

Preferably, the benzylaminopurine, TDZ and IAA are each (individually, not in combination) applied at a rate of less than about 1000 ppm, less than about 900 ppm, less than about 800 ppm, less than about 700 ppm, less than about 600 ppm, less than about 500 ppm, less than about 400 ppm, less than about 300 ppm, less than about 200 ppm, less than about 100 ppm, less than about 90 ppm, less than about 80 ppm, less than about 70 ppm, less than about 60 ppm, less than about 50 ppm, less than about 40 ppm, less than about 30 ppm, less than about 20 ppm or less than about 10 ppm.

The method for altering rhizome architecture is particularly suited to the rhizomes of *Miscanthus* plants, but may also be used for other rhizomatous plants.

The combinations and concentrations of plant hormones may readily be optimized, if necessary, by one skilled in the art depending on the plant to be propagated. The resulting mini rhizomes or mini stem cutting having modified architecture may then be used in a method for the production of a plant, comprising the steps of growing a rhizome or an encapsulated rhizome or a mini stem cutting or encapsulated mini stem cutting obtainable by the aforementioned methods for altering rhizome or mini stem architecture.

According to another aspect of the present invention, there is provided use of benzylaminopurine, TDZ and IAA to modify the architecture of rhizomes, particularly *Miscanthus* rhizomes, or to modify the architecture of mini stems.

According to another aspect of the present invention, there is provided use of benzylaminopurine, TDZ and IAA to increase the yield of rhizomatous plants or the yield of plants propagated using stem cuttings compared to the yields obtained using conventional production methods. The use of benzylaminopurine, TDZ and IAA is as described above in the method for plant propagation.

In such use, the benzylaminopurine, TDZ and IAA are each (individually, not in combination) applied at a rate of less than about 1000 ppm, less than about 900 ppm, less than about 800 ppm, less than about 700 ppm, less than about 600 ppm, less than about 500 ppm, less than about 400 ppm, less than about 300 ppm, less than about 200 ppm, less than about 100 ppm, less than about 90 ppm, less than about 80 ppm, less than about 70 ppm, less than about 60 ppm, less than about 50 ppm, less than about 40 ppm, less than about 30 ppm, less than about 20 ppm or less than about 10 ppm.

The architecture of the rhizomes and mini stem cuttings is modified such that the resulting mini rhizomes or mini stem cuttings after application of the plant hormones are substantially uniform in shape and weight less than about 25 g or weigh less than about 20 g or weigh less than about 15 g or weigh less than about 10 g or weight less than about 5 g or weigh less than about 2 g.

According to a further aspect of the present invention, there is provided a coating for a propagule comprising a biodegradable polymer, which preferably has a melting point of between 30 to 65° C. The invention also provides propagules coated with such a biodegradable polymer.

Preferably the propagule is encapsulated prior to being coated in the biodegradable polymer. The propagule may advantageously be encapsulated in any plant growth medium, such as compost, potting mix, peat, hydrogel, soil, rock wool, perlite, vermiculite, foam, syrofoam, pumice, coir, expanded clay pellets etc. The encapsulation material may also comprise compounds, such as plant hormones (such as cytokinins or auxins), plant growth regulators, mycorrhiza, endophytic organisms, symbiotic organisms or other beneficial organisms, surfactants, gels, fungicides, nematicides, insecticides, organic and inorganic nutrients, water, polymer and organic based super absorbents and stabilization compounds etc. to aid the storage of the propagule so as to prevent any loss of material due to deterioration and to enhance the survival and performance of the propagules once they are planted in the field.

Preferably the polymer is one or more of wax, polyester, petroleum-based paraffin or plastic, polysaccharide or any plant-based plastic.

The coating may comprise Preferably, the coating also comprises a fibre, which may comprise at least up to 20%, at least up to 30%, at least up to 40%, at least up to 50%, at least up to 60%, at least up to 70%, at least up to 80% or at least up to 90% of the coating.

The fibre may be one or more of the following (i) fibre from agricultural biomass residue (for example, cereal straw, cotton, peanut hulls, soy straw, corn fodder); (ii) dedicated fibres (for example, *Miscanthus, Arundo*, sugarcane, bagasse, hemp, Kenaf); (iii) processed fibres (for example, paper, recycled cardboard, wood flour, wood saw dust); and (iv) artificial or processed fibres (for example, nylon, polyester, cotton).

The coating may also comprise fungicides, endophytic organisms, plant nutrients, hormones, dyes or other means for identification, such as barcodes or transponders or the like, to aid sorting.

The coating is applied to the (encapsulated) propagule by, for example, dipping (at least once) or by co-extrusion or by thermally forming the coating around the propagule. The coating covering the (encapsulated) propagule is less than 1 mm (millimetre) thick, preferably less than 0.5 mm thick.

According to a further aspect of the present invention, there is provided use of a biodegradable polymer, which preferably has a melting point of between 30° C. to 65° C., for the coating of a propagule.

A "propagule" as defined herein is any plant part which is capable of being grown or regenerated into a whole plant. A propagule may therefore comprise, rhizomes, mini rhizomes, stem cuttings, mini stem cuttings, tubers, seeds etc.

In the case where the propagule is a seed, any commercial or other seed variety may optionally first be encapsulated as described above and then coated in a biodegradable polymer as described. The seed may be a transgenic or non-transgenic seed. Preferred seeds include melon and tomato seeds.

FIGURES

The present application will now be described with reference to the following Figures which are by way of illustration alone, in which.

EXAMPLES

Figure 1A:
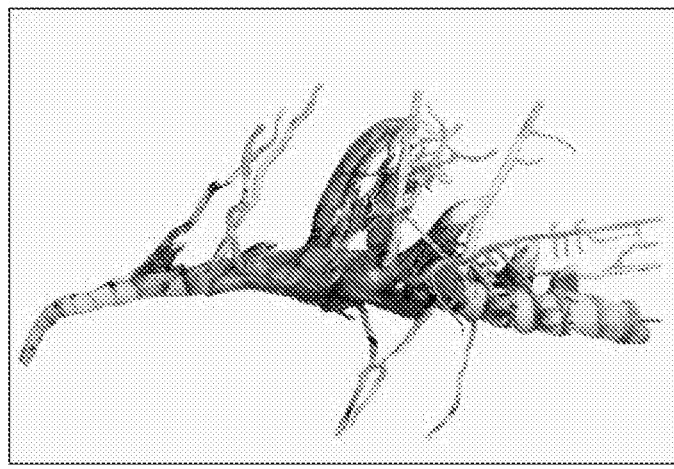
FIG. 1a shows a rhizome from *Miscanthus* produced by conventional methods (weighing about 30 g) and FIG. 1b shows a mini rhizome from *Miscanthus* produced by the methods of the present invention (weighing around 2 g).
Figure 1B:
Figure 2:
FIG. 2 shows *Miscanthus* plantlets undergoing micro-propagation according to stage (i) of the method of the invention.
Figure 3:
FIG. 3 shows the crop establishment in the field of *Miscanthus* plants produced from the encapsulated mini rhizomes (right hand half of the picture) produced by the methods of the present invention compared to plant produced from conventional rhizomes (left hand half of the picture).

The present application will now be described with reference to the following examples.

Example 1: Micropropagation and Multiplication of *Miscanthus*

Explant material was selected from disease-free *Miscanthus* plant material. The explant material was surface sterilized, rinsed in sterilized water and seeded onto an agar-based growth medium containing nutrients (sucrose and other standard nutrients) and plant hormones to encourage cell division. The resulting callus was then re-plated onto a growth medium infused with nutrients and plant hormones (cytokinins and auxins) to stimulate cell differentiation into roots and shoots and the production of plantlets. Repeated cycles of this process allow a single explant sample to be increased from one to thousands of plantlets.

Example 2: Hormone Manipulation

The plantlets were then planted in compost and grown in a greenhouse until 5 to 10 shoots were established. The plantlets were then subjected to a temporary drought by withholding watering of the plants for a period of 1 day. The shoots, when about 10 cm tall, were subjected to a separation procedure which involved separating, by hand, each shoot having a dedicated root system and potting this shoot into compost. The potted shoots were then treated with a combination of benzylaminopurine, TDZ and IAA each being at a rate of <1000 ppm (less than one thousand parts per million) to enhance shoot and root initiation.

After about 30 to 45 days, the aboveground plant tissue was removed and the rooting systems removed from the pots and lightly separated. These mini rhizomes were then ready for the encapsulation process described in Example 4 below.

Example 3: Using Mini Stem Cuttings

*Arundo donax* (giant reed), *Pennisetum purpureum* (napier grass) and energy cane are more suited to multiplication using stem cuttings. The *Arundo donax, Pennisetum purpureum*, sugarcane and energy cane plantlets were subjected to micro-propagation and multiplication as described in Example 1. Plantlets derived from micro-propagation and multiplication were planted onto compost and grown to a height of about 10 cm. The aboveground growth was cut back to a point just above a node to encourage more bud formation, which was further stimulated by the application of benzylaminopurine, TDZ and IAA, each being at a rate of <1000 ppm (less than one thousand parts per million). Shoots emerging from the new buds were removed and cut by machine into short lengths to form mini stem cuttings. These mini stem cuttings were then encapsulated as described in Example 4.

Example 4: Encapsulation

Encapsulation was carried out using machinery available in the horticultural industry for encapsulating seeds or cuttings but adapted so as to fully encase the mini-rhizome or mini stem cutting. The mini-rhizome or stem cutting was introduced into a flow of compost containing cytokinins, auxins, mycorrhiza, surfactants, gels, fungicides and insecticides. The compost surrounding the mini-rhizome or stem cutting was then compressed. The resulting unit of mini-rhizome or mini stem cutting in compressed compost was then wrapped in a paper binding to increase the stability of the encased propagule. The encased propagule was then stored until required for planting.

The invention claimed is:

1. A method for increasing bud formation in mini rhizomes or mini stem cuttings, comprising the steps of:
    (i) contacting a plantlet or a part thereof previously produced via micro-propagation of plant material from a vegetatively reproducing plant followed by multiplication with at least one plant hormone to encourage root and shoot initiation, wherein said at least one plant hormone is selected from auxins and/or cytokinins;
    (ii) exposing the plantlets after step (i) to two or more separate occasions of a temporary abiotic stress and temporary mechanical stress for periods effective to increase bud formation, wherein said temporary stresses comprise exposure to each stress between non-stress periods, wherein said abiotic stress includes any one or more of an osmotic stress, a temperature stress, a nutrient stress, or an oxidative stress, and wherein said mechanical stress comprises cutting back aboveground parts of a plant to a point just above a node;
    (iii) growing the plantlets and harvesting mini rhizomes or mini stem cuttings therefrom, wherein said mini rhizomes or mini stem cuttings weigh less than about 15 grams; and
    (iv) encapsulating said mini rhizomes or mini stem cuttings produced from step (iii) in a plant growth medium to provide an encapsulated mini rhizome or an encapsulated mini stem cutting.

2. The method according to claim 1, wherein said encapsulated mini rhizome or mini stem cutting is coated in a biodegradable polymer.

3. The method according to claim 2, wherein said biodegradable polymer has a melting point of between 30 to 65° C.

4. The method according to claim 2, wherein said biodegradable polymer comprises one or more of wax, polyester, petroleum-based paraffin or plastic, polysaccharide or any plant-based plastic.

5. The method according to claim 2, wherein said coating comprises a fibre component of at least 20% of the coating.

6. The method according to claim 5, wherein said fibre comprises one or more of the following: (i) fibre from agricultural biomass residue; (ii) fibres from dedicated fibre crops; (iii) artificial or processed fibres.

7. The method according to claim 2, wherein said coating comprises one or more of the following: fungicides, endophytic organisms, plant nutrients, hormones, dyes, barcodes or transponders.

8. The method according to claim 1, wherein said vegetatively reproducing plant is a plant propagated using a stem cutting.

9. The method according to claim 8, wherein said plant is selected from *Miscanthus* (elephant grass), *Pennisetum purpureum* (napier grass), *Panicum virgatum* (switch grass), energy cane (the *Saccharum* complex), *Arundo donax* (giant reed), sugarcane, *Bambusa* (bamboo), *Curcuma*, *Humulus* (hop), asparagus, *Zingiber* (ginger), iris, genus *Erianthus*, *Fallopia sachalinensis* (Igniscum), strawberry (Genus *Fragaria*), herb Nettle (Genus *Urtica*), *Hevea* (rubber) and *Manihot* (cassava), turmeric, wasabi and *Ipomoea batatas* (sweet potato).

10. The method according to claim 1, wherein said abiotic stress is an osmotic stress.

11. The method according to claim 1, wherein said plant hormones comprise at least one of benzylaminopurine, TDZ and IAA.

12. An encapsulated mini rhizome or mini stem cutting obtained by the method according to claim 1.

13. An encapsulated mini rhizome or mini stem cutting according to claim 12 coated in a biodegradable polymer.

14. A planting unit weighing less than about 25 g, comprising an encapsulated mini rhizome or encapsulated mini stem cutting produced according to the method of claim 1 and optionally coated in a biodegradable polymer.

15. A propagule having increased bud formation obtained by
  (i) contacting a plantlet or a part thereof produced via micropropagation of plant material from a vegetatively reproducing plant followed by multiplication with at least one plant hormone;
  (ii) exposing the plantlets after step (i) to two or more separate occasions of a temporary abiotic stress and temporary mechanical stress for periods effective to increase bud formation, wherein said temporary stresses comprise exposure to each stress between non-stress periods, wherein said abiotic stress includes any one or more of an osmotic stress, a temperature stress, a nutrient stress, or an oxidative stress, and wherein said mechanical stress comprises cutting back aboveground parts of a plant to a point just above a node;
  (iii) growing the plantlets and harvesting mini rhizomes or mini stem cuttings therefrom, wherein said mini rhizomes or mini stem cuttings weigh less than about 15 grams and have increased buds;
  (iv) encapsulating said mini rhizomes or mini stem cuttings produced from step (iii) in a plant growth medium; and
  (v) coating the encapsulated mini rhizomes or mini stem cuttings in a biodegradable polymer to form a propagule.

16. The propagule according to claim 15, wherein the propagule is encapsulated in a plant growth medium before being coated in a biodegradable polymer.

17. The propagule according to claim 15, wherein said biodegradable polymer has a melting point of between about 30 to about 65° C.

18. The propagule according to claim 15, wherein said biodegradable polymer is selected from one or more of wax, polyester, petroleum-based paraffin or plastic, polysaccharide or any plant-based plastic.

19. The propagule according to claim 15, wherein said coating comprises a fibre component of up to 20% of the coating.

20. The propagule according to claim 19, wherein said fibre comprises one or more of the following: (i) fibre from agricultural biomass residue; (ii) fibres from dedicated fibre crops from one or more of *Miscanthus*, *Arundo*, sugarcane, bagasse, hemp, and Kenaf; or (iii) artificial or processed fibres.

21. The propagule according to claim 15, wherein said coating comprises one or more of the following: fungicides, endophytic organisms, plant nutrients, hormones, dyes, barcode or transponder.

22. The propagule according to claim 15, wherein said coating is applied to the encapsulated propagule by dipping, co-extrusion or by thermally forming the coating around the propagule.

23. The method according to claim 1, wherein the mini-stem cuttings weigh less than 5 g.

24. A mini stem cutting obtained by a method according to claim 23.

25. A method for the production of a plant, comprising the steps of growing an encapsulated mini rhizome or mini stem cutting obtained by a method according to claim 1.

26. A method for production of bio-fuels or bioethanol, the method comprising growing a plant from the propagule of claim 15.

27. A method for bioremediation, the method comprising growing a plant from the propagule of claim 15.

28. A method for altering the harvest cycle of a plant, the method comprising growing a plant from the propagule of claim 15.

29. The method according to claim 1, wherein there are three or more separate occasions of a temporary abiotic stress and temporary mechanical stress.

30. The method according to claim 1, wherein there are four or more separate occasions of a temporary abiotic stress and temporary mechanical stress.

* * * * *